(12) United States Patent
Iseri et al.

(10) Patent No.: US 6,451,212 B2
(45) Date of Patent: Sep. 17, 2002

(54) METHOD OF TREATING WATER IN A WATER SYSTEM

(75) Inventors: Hajime Iseri; Yutaka Yoneda; Kuniyuki Takahashi, all of Tokyo (JP)

(73) Assignee: Kurita Water Industries Ltd., Tokyo (JP)

( * ) Notice: Subject to any disclaimer, the term of this patent is extended or adjusted under 35 U.S.C. 154(b) by 0 days.

(21) Appl. No.: 09/947,469

(22) Filed: Sep. 7, 2001

Related U.S. Application Data

(63) Continuation of application No. PCT/JP00/08476, filed on Nov. 30, 2000.

(30) Foreign Application Priority Data

Feb. 14, 2000 (JP) ........................................ 2000-035544

(51) Int. Cl.⁷ .................................................. C02F 1/50
(52) U.S. Cl. ........................................ 210/746; 210/764
(58) Field of Search ................................ 210/746, 764, 210/85

(56) References Cited

U.S. PATENT DOCUMENTS 4,839,580 A * 6/1989 Moore et al.
5,820,763 A * 10/1998 Fujita et al.
5,977,782 A * 11/1999 Kordecki et al.
6,001,264 A * 12/1999 Suzuki et al.
6,077,418 A * 6/2000 Iseri et al.

FOREIGN PATENT DOCUMENTS

| JP | 11-28474 | 2/1999 |
| JP | 11-118703 | 4/1999 |
| JP | 2000-9674 | 1/2000 |
| JP | 2000-28516 | 1/2000 |

* cited by examiner

Primary Examiner—Betsey Morrison Hoey
(74) Attorney, Agent, or Firm—Kanesaka & Takeuchi

(57) ABSTRACT

According to the method of treating water in a cooling water system, adhesion of fouling is on-line monitored by a compact and inexpensive apparatus and a slime control treatment is intensified according to the result of on-line monitoring. The water treatment is intensified in response to the change of electric potential of a sensor monitoring microbial fouling 11 made of sensitized metallic material. When the electric potential of the sensor exceeds a threshold value, an agent is added through both chemical feeding pumps 15 and 17. When the electric potential lowers to the normal value, the agent is added only through the pump 15.

11 Claims, 3 Drawing Sheets

METHOD OF TREATING WATER IN A WATER SYSTEM

CROSS REFERENCE TO RELATED APPLICATION

This is a continuation application of PCT/JP00/08476 filed on Nov. 30, 2000.

FIELD OF THE INVENTION

The present invention relates to a method of treating water in a water cooling system, pulp manufacturing process, and so on, in which microbial fouling on a metal pipe and the like contacting water is monitored and an appropriate water treatment is carried out based on the result of monitoring. More particularly, the present invention relates to a water treatment system in which microbial fouling on a metal pipe and the like is predicted early and precisely by monitoring change of corrosion potential of a sensor having a sensitized metal and contacting the water, and thus an appropriate water treatment is carried out based on the prediction.

BACKGROUND OF THE INVENTION

Some problems of a water system are associated with slime. Slime which is formed by microbes in water causes decreasing a heat transfer efficiency of a heat exchanger, clogging of pipes, and corrosion of pipes and the like. To prevent such problems, various slime control treatments are done; for example, a microbicide is added into the water system. Moreover, according to an amount of slime adhered on the pipes, a slime removing agent is added into the water to eliminate slime adhered on pipes and the like ("Manual for Protecting Pipes from Corrosion", edited by Kajima Construction Co., Ltd. and Kurita Water Industries Ltd., and published by Nippon Kogyo Publishing Company in 1987).

According to a conventional method of monitoring microbial fouling in a water system, a rubber plate is immersed in water of a water system, and the rubber plate is measured periodically on an amount of a fouling component adhered to the rubber plate. Another method is disclosed in NACE Standard RPO189-89, "Standard Recommended Practice On-line Monitoring of Cooling waters", NACE International, Houston, 1996, in which microbial fouling is detected by a change of pressure difference in a tube.

In natural seawater, stainless steel becomes to have an extremely high corrosion potential when microbes adhere thereto (R. Johnsen, Corrosion, 41:296, 1985). The same phenomenon occurs in a cooling water system (Hirano et. al: 38th corrosion-corrosion prevention debate, 1991).

Japanese patent publication H6-201637A and Japanese Patent 2794772 disclose methods of monitoring microbial fouling by measuring a natural electrode potential. Japanese patent publication H10-142219A and Japanese patent publication 2000-9674A disclose a method of controlling addition of an agent based on measured results of a corrosion potential.

In a conventional slime control treatment, an appropriate slime control agent is selected for a water system and an amount of the agent to be added is predetermined or controlled so that the concentration of the agent in the water system would be in a predetermined range. Lately, a slime control treatment has been carried out with using a controlling apparatus to meet the requirements of ecology, safety handling, better workability, and so on. However, because of various external factors such as the deterioration of water quality, a sufficient treatment may not be accomplished by adding usual amounts of agents or by controlling concentrations of agents in the water system. Then, microbial fouling adhere to the system and cause various problems.

In order to prevent such problems, more amount of a slime controlling agent may be added according to a fouling level of a water system which is measured by monitoring adhesion of contaminants. It is desirable to monitor the adhesion of fouling all the time and to add more amount of slime controlling agent soon after the adhesion of fouling is detected. However, at the present time, the slime controlling agent is increased in its additive amount manually based on the fouling level monitored from time to time.

It is desirable to control the addition of agents automatically based on the result of on-line monitoring. However, the aforementioned method using a rubber plate can not be an on-line monitoring method.

The other aforementioned method measuring differential pressure of a tube can be an on-line monitoring method. However, a fouling level measured as a change of the differential pressure is considerably affected by the way of adhesion of fouling elements to a tube, that is, whether the fouling elements adhere to the tube evenly or unevenly. Furthermore, there is an disadvantage to install a monitor of this type in each cooling water system. In addition, expensive parts such as a differential pressure gauge must be equipped and a monitoring apparatus needs a large space to be installed because the tube needs enough length for measuring differential pressure. Since a differential pressure should be measured under a condition of a constant flow velocity of cooling water in a tube, the water flow in the tube is adjusted by a constant flow valve or the like. An obtained value of differential pressure is often affected by a small change in the flow velocity caused by fouling in the valve.

The surface of a plate sensor used in a conventional method of monitoring the corrosion potential is so smooth that its sensitivity is not good enough.

As mentioned above, there are a lot of problems in each conventional method in which the addition of agents or the operation of an apparatus is controlled based on the monitoring result of microbial fouling.

When a slime control treatment is not accomplished sufficiently and a large quantity of slime adheres to a water system, the slime should be removed off. However, when the water system is not monitored all the time, the fouling level in the system is unclear and the slime is retained in the water system for a long time.

When slime is removed from the water system by adding a removing agent automatically at regular intervals controlled by a timer, the water system is saved from fouling. However, in this case, the removing agent may be added even if there is no fouling. That is a waste of the agent. A necessary treatment should be done at a necessary time to reduce treatment cost and to meet the ecological requirements.

SUMMARY OF THE INVENTION

It is an object of the present invention to provide a method of water treatment in which microbial fouling onto metallic pipes and the like is detected early and precisely and an appropriate water treatment is carried out according to the detection.

A method of water treatment in a water system of the present invention employs at least one sensor having a sensitized metal piece for monitoring microbial fouling, and the water is treated according to a change of electric potential of the metallic sensor.

DESCRIPTION OF THE PREFERRED EMBODIMENTS

Figure 1:
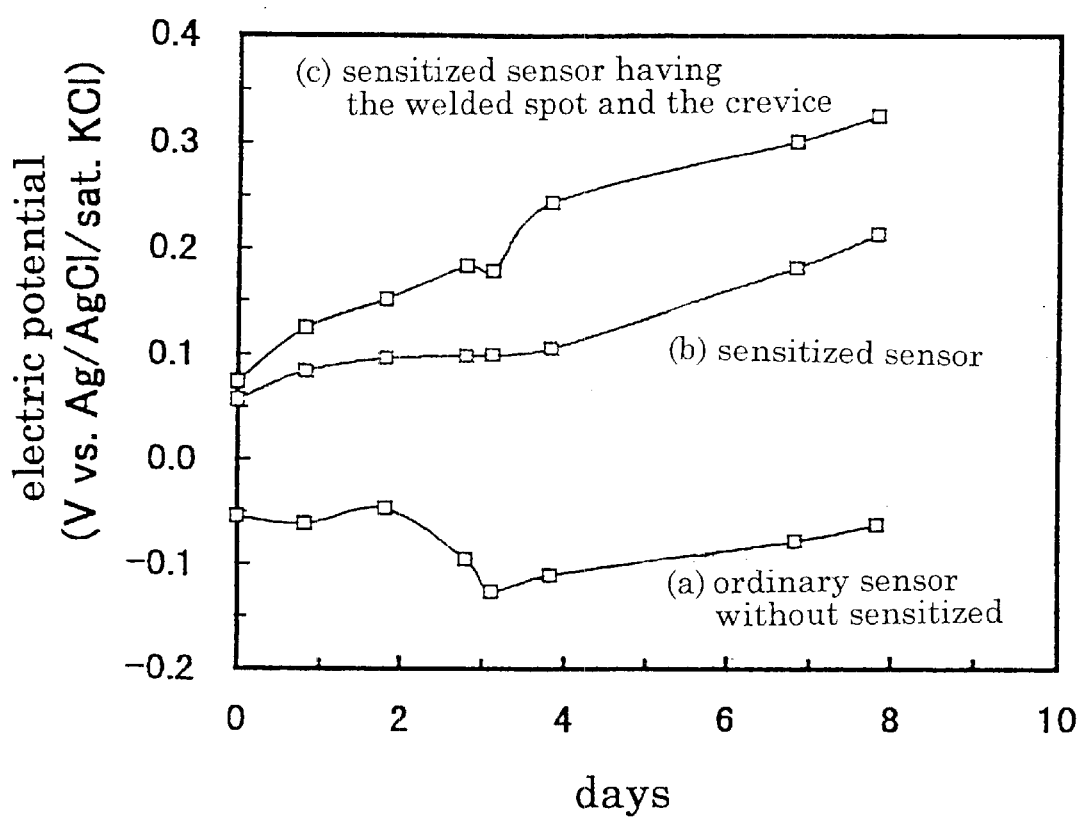
FIG. 1 shows sensitivities to microbial fouling of test pieces in Example 1.

A monitoring sensor for detecting fouling caused by microbes is made of sensitized metallic material. The metal may be sensitized by annealing it in an electric furnace, but it can be sensitized by another method. The sensitized metal may be a metallic piece having at least one welded spot and at least one crevice. Such a metallic piece with a crevice can detect the microbial fouling with a very high sensitivity.

The metal to be sensitized may be stainless steel or nickel alloy, but is not limitative thereto.

A metallic piece with a crevice for a sensor may be prepared by overlapping two plates of the same kind of metal each other and welding them so as to make at least one welded spot and at least one crevice. The metal pieces may have any shape.

The plates may be welded by spot welding, but not limitative thereto. It is recommended to use a metallic piece having no expulsion in welding. Two metallic pieces are preferably welded at 1 to 3 spots.

The welded plates with a crevice may have a surface area excluding welded area larger than a welded area. It makes no difference if post weld treatments (stress relief and so on) are done around a welded area or not. An opening width of an air gap between two welded metallic plates is preferably one tenth of an opening depth or smaller.

Coated wire may be connected to the sensitized metallic plate of the sensor and an electric potential is measured via this coated wire. The metallic plate may be connected with the coated wire through a solderless terminal which is attached to the coated wire and screwed on the metallic plate. Instead thereof, the metallic plates may be connected with the coated wire by soldering or the like.

When the water temperature in a water system is in a range that microbes can grow, the metallic material of the sensor does not need to be heated. When the water temperature in the water system is too low for the growth of microbes, a heating plate may be attached to the metallic plate of the sensor in order to stimulate the growth of microbes on the surface of the sensor. The temperature of the surface of the sensor contacting the water is preferably in a range of 5–50° C., more preferably in a range of 10–40° C.

When the metallic plate of the sensor has the crevice described above, the heating plate is preferably attached to the exterior surface of the larger metallic plate of two. When the area of the two metallic plates are equal, the heating plate can be attached to either one.

The surface of the heating plate may be coated with insulating resin or the like to electrically insulate the heating plate from the metallic material of the sensor.

When the heating plate heats the metallic plate of the sensor in water, heating surface of the plate has preferably a temperature in a range where microbes can grow, preferably in a range of 10–50° C. In order to keep the temperature in the above range, the heating plate is preferably equipped with a thermostat such as a liquid expansion thermostat, a bimetal thermostat, a temperature controlling system using a thermocouple temperature sensor, and the like. The heating plate may be composed of an electric resistance composition having a positive temperature coefficient (PTC), that is, a property of having a drastic change in electric resistance responding to a change in temperature. When the sensor is provided with the heating plate composed of the composition having the positive temperature coefficient (PTC); an exterior temperature sensor is not necessary, the amount of electric power consumption is small, and it is not overheated even in a failure.

The size and shape of the heating plate are determined according to those of the surface of the metallic plate to which the heating plate is attached.

The heating plate can be attached to the metallic plate with an adhesive, a double-sided tape, or the like. The adhesive should not be degraded by heat from the heating plate.

It is preferable that the sensitized metallic plate of the sensor is in contact with water only at a part thereof for monitoring, and that other part of the metallic plate is not in contact directly with water. Accordingly, the other part of the metallic plate is preferably coated with insulating resin such as silicone resin at its entire surface except for the area for monitoring the potential.

The electric potential of the sensor having the sensitized metallic plate rises when microbial fouling adheres thereto in a water system. This phenomenon is also observed in a metallic plate which is made of the same kind of metallic material but not sensitized. However, the unsensitized plate has much lower sensitivity for fouling than that of the sensitized plate. Particularly, sensitized metallic plates having the welded spot(s) and the crevice is extremely sensitive to the fouling and detects microbial fouling with a very high sensitivity so as to make it possible to perform an appropriate slime control treatment.

When the sensor is in contact with water in a water system which is treated properly by a slime controlling treatment, an electric potential of the sensor is almost constant. When the slime controlling treatment is not appropriate, the electric potential of the sensor tends to rise. When a tendency of rising potential is detected, the slime controlling treatment is controlled automatically so as to treat the water system more sufficiently. For example, when the electric potential of the sensor exceeds a threshold value, the slime controlling treatment is intensified, or an apparatus for eliminating the microbial fouling is started to operate.

Examples of the apparatus for eliminating microbial fouling include an apparatus having a membrane for eliminating microbes, an apparatus which sterilizes microbes by ultraviolet light, and an apparatus which adds at least one chemical for sterilizing microbes such as ozone, chlorine, hypochlorous acid, hydrogen peroxide, chlorine dioxide, active oxygen in the form of the radical species, and the like.

A threshold value can be determined suitably according to a value of the electric potential which is observed right after the sensor is immersed in a water system, that is, when the sensor is not affected by fouling in the water system. It is preferable to set the threshold value in a range of 100–300 mVvs.Ag/AgCl/sat.KCl for a usual cooling water system.

For intensifying the slime controlling treatment, it is desirable to add a larger amount of the agent than usual or to add another kind of agent additionally together with the agent usually used. When the usual slime controlling agent is added continuously by a chemical feeding pump, an larger amount of the agent can be added only by increasing the amount of the agent, or by installing another chemical feeding pump to add an extra amount of the agent in addition to the pump in the ordinary operation. An extra amount of the agent can be added either continuously or intermittently. When the slime controlling agent is intermittently added at a usual operation, a larger amount of the agent than usual can be added by increasing the frequency of addition of the agent, or by increasing an amount of the agent added at one time.

When another kind of slime controlling agent which is different from the ordinary one is added additionally, it is desirable to install a chemical feeding pump for the other agent and to control it according to a signal from the sensor. The agent can be added either continuously or intermittently. Both the treatments, adding the agent and eliminating the microbial fouling by the apparatus, can be carried out at the same time. Or either one of them can be carried out.

The intensified slime control treatment is continued until the value of the electric potential signaled from the sensor lowers to the value of normal electric potential, that is, the value of electric potential of the sensor not affected by fouling. The value of the normal electric potential can be set according to the water system.

A method of the releasing slime includes installing a pump and adding a predetermined amount of an agent for releasing slime in batch operation. The release treatment is usually carried out only once.

When the electric potential of the sensor does not lower to the normal electric potential for a definite period of time after the treatment is started to be intensified or after the release treatment is started, an emergency signal is preferably sent.

Once the emergency signal is sent, a malfunction of the sensor is checked, and furthermore, a fouling level in the water system is estimated from the result of water analysis, other monitoring methods, and so on. When it becomes certain that fouling in the water system is serious, it is necessary to perform a further release treatment and to take a drastic measure.

Adding an oxidizing agent such as chlorine for the slime control treatment may cause a problem in monitoring microbial fouling because the electric potential of the sensor depends on the concentration of the oxidizing agent. However the method of the water treatment of this invention can be applied to a water system in which an oxidizing agent is added as the slime control agent, if the concentration of the oxidizing agent in the water system is kept constant. An example of the method to keep the concentration of the oxidizing agent constant is monitoring the concentration of the oxidizing agent automatically and adjusting an amount of the oxidizing agent to add according to the result of monitoring.

An oxidizing agent can be added to intensify the slime control treatment. However, the electric potential of the sensor may be affected by the concentration of the oxidizing agent when it becomes high and there may be a concern about the corrosion of materials in the system. Accordingly, it is preferable to add a non-oxidizing agent instead of the oxidizing agent. Even in a case that an apparatus is used to eliminate microbial fouling, the oxidizing agent is controlled desirably to be kept at a low concentration.

The electric potential of the sensor can be detected by any method. A chemical feeding pump and an apparatus for eliminating the microbial fouling can be controlled by any controlling system. The system may include a computer. It is preferable to measure the electric potential of the sensor not less than 6 times a day, but not limitative thereto.

It is desirable to exchange the sensor to a new one periodically, at least once a year. It is also desirable to exchange the sensor after an emergency signal is detected.

There is no limitation to the number of sensors to be installed. Two or more sensors can be installed to detect the electric potential at an improved precision. The sensors having different sensitivities, for example, a sensor made of sensitized metallic material of this invention and a sensor made of not sensitized metallic material, make it possible to perform the intensified treatment more appropriately. Water treatment can be intensified when a rise of electric potential occurs in the sensitive sensor followed by a rise in the less sensitive one.

EXAMPLE 1

The sensitivities of the sensors to microbial fouling were measured and the results are shown in FIG. 1.

Contaminants including slime collected in a practical water cooling system was added into circulating cooling water having a temperature of 30° C. to prepare sample water. Three kinds of test pieces A, B, and C in the following were immersed into the sample water and electric potentials of them were measured;

A: a test piece made of type 304 stainless steel (SUS304),

B: a test piece made of SUS304 sensitized at 650° C. for 24 hours, and

C: a test piece having a crevice prepared by joining two metal plates in different sizes made of SUS304 through spot welding followed by sensitizing at 650° C. for 24 hours.

As shown in FIG. 1, after immersed into the sample water, the electric potential of the test piece C rose at a high rate. The electric potential of the test piece B rose at a low rate. The electric potential of the test piece A had just slight changes during this experiment.

This means that the sensitivity of the sensitized metallic material to microbial contaminants is high and that of the sensitized metallic sensor with a crevice is even higher.

It was confirmed that the electric potential of the test piece A, B, or C did not have any drastic changes while the test piece was immersed into the water system containing no contaminant.

EXAMPLE 2

Figure 2:
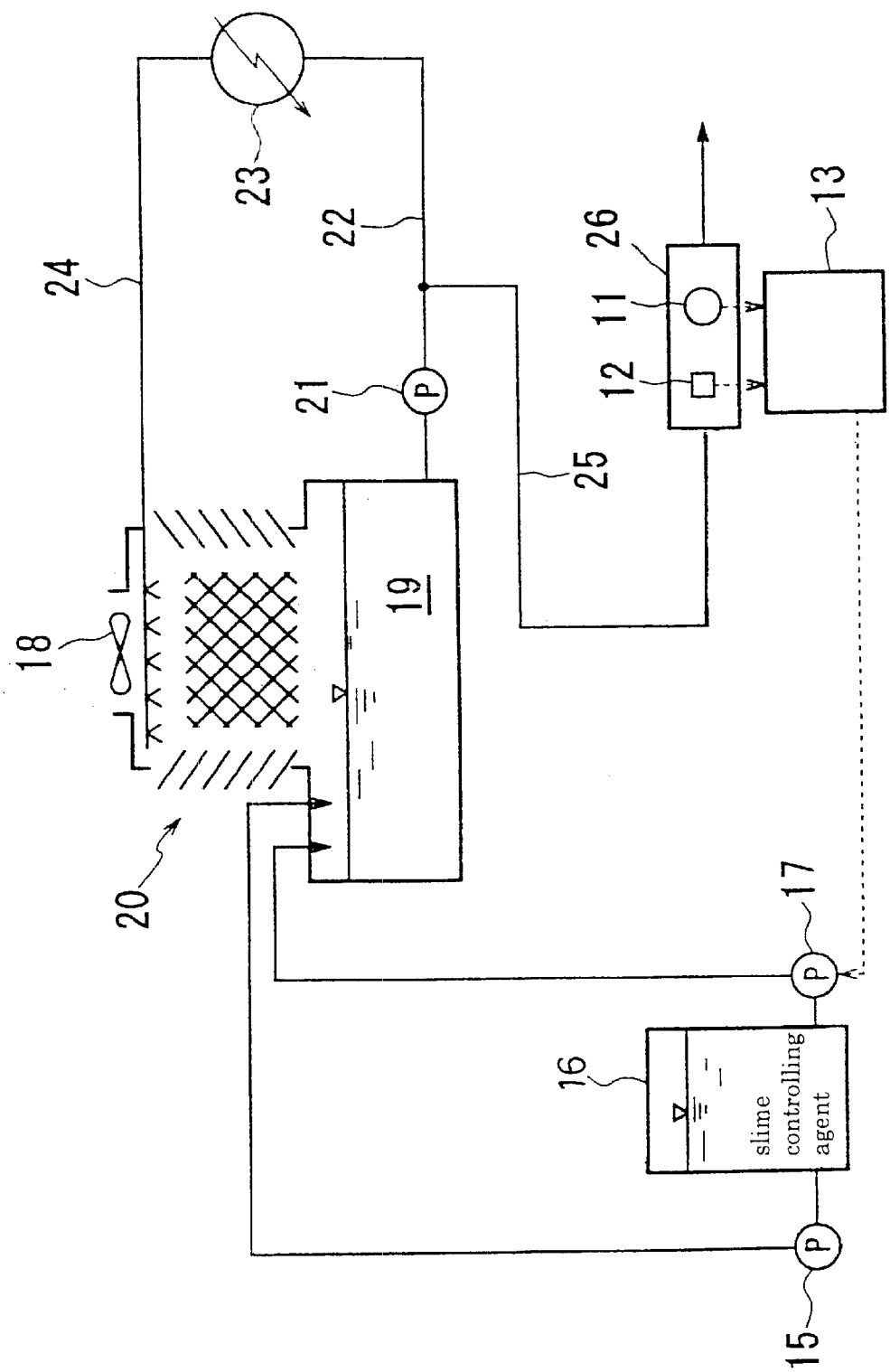
FIG. 2 is a schematic diagram of a cooling water system used in Example 2.

In a model plant of a cooling water system shown in FIG. 2, a corrosion potential of metal (SUS304) was monitored by detecting the electric potential of the test piece C of Example 1 immersed in the cooling water, and the water treatment was carried out based on the result of monitoring.

In the water system, water in a cooling tower 20 having a cooling fan 18 and a pit 19 was sent to a heat exchanger 23 via a water pump 21 and a pipe 22 and returned to the cooling tower 20 via a pipe 24. A pipe for collecting sample water 25 was branched off from the pipe 22. Collected sample water having a temperature of 30° C. was sent to a test tube 26 via the pipe 25 and returned to the cooling tower 20 or to the pipe 22 or 24.

The test tube 26 had a sensor 11 and a reference electrode (Ag/AgCl/sat.KCl electrode) 12. Signals from the sensor 11 and from the reference electrode 12 were sent to a control device 13. The control device 13 measured an electric potential of the sensor 11 referring to an electric potential of the reference electrode 12. Controlling signals from this control device 13 were sent to a chemical feeding pump 17.

A slime control agent in a tank 16 is added into the pit 19 by chemical feeding pumps 15, 17.

When the sensor 11 did not detect fouling, the agent was added only through the chemical feeding pump 15 for ordinary use. When the sensor 11 detected fouling, the agent was added through both pumps 15 and 17 in order to intensify the slime control treatment.

Figure 3:
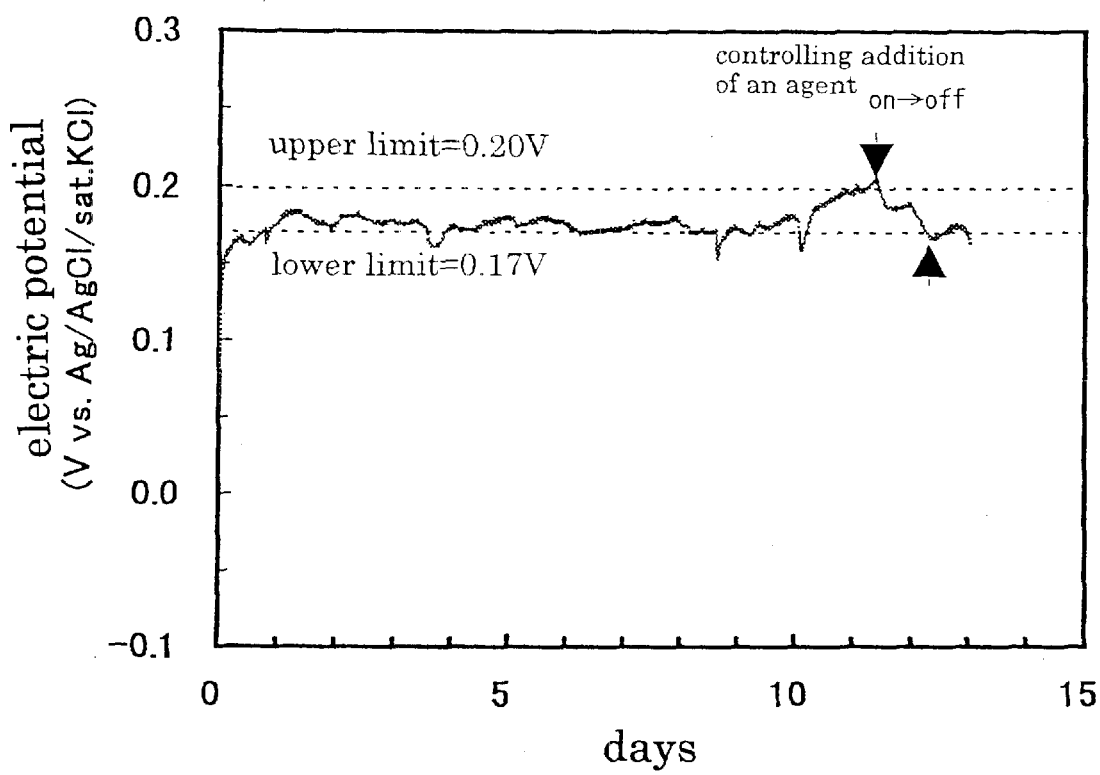
FIG. 3 shows the change of corrosion potential with the passage of time when the method in Example 2 is carried out.

FIG. 3 shows changes in the electric potential of the sensor 11 with the elapsed time under the experimental condition that the chemical feeding pump 15 was stopped and contaminants including slime collected in a practical cooling water system regularly. The electric potential exceeded the upper limit (0.20V) on the eleventh day since the experiment started, and an organic slime control agent was added automatically through the pump 17. The electric potential lowered to the lower limit (0.17V) in about a day and then the pump 17 stopped adding the slime control agent automatically.

INDUSTRIAL APPLICABILITY

The system of the present invention detects the microbial fouling by the sensor precisely and performs the slime control treatment appropriately by controlling an additive amount of the agent(s) or by controlling the apparatus for the treatment, and thus the condition of the water system is kept good.

According to the method of the present invention, the compact and inexpensive on-line monitor monitors the fouling, and the slime control treatment can be intensified based on the result of monitoring. Fouling by slime in the water system can be prevented by detecting the fouling early and perform the treatment promptly. Furthermore, since the slime control treatment is intensified only at a necessary time, no agent is wasted and the effect of the agent on the environment can be minimized. With respect to the treatment by an apparatus, the apparatus is operated only if necessary to decrease the amount of the power consumption and to lower the maintenance cost.

What is claimed is:

1. A method of treating water in a water system including steps of monitoring the water system by a sensor and treating the water based on the result of monitoring,
   wherein said sensor includes metallic material sensitized and monitors microbial fouling adhered thereon, and
   the water is treated according to the change of electric potential of the sensor.

2. A method as claimed in claim 1, wherein the metallic material has at least one welded spot and at least one crevice.

3. A method as claimed in claim 1, wherein the water is treated by adding at least one agent into the water system.

4. A method as claimed in claim 3, wherein the agent includes at least one slime control chemical.

5. A method as claimed in claim 3, wherein the additive amount of the slime control agent is increased when the electric potential of the sensor exceeds a predetermined value.

6. A method as claimed in claim 3, wherein another slime control agent different in kind from the ordinary one is added into the water system when the electric potential of the sensor exceeds a predetermined value.

7. A method as claimed in claim 1, wherein the water is treated by an apparatus for eliminating microbial fouling.

8. A method as claimed in claim 7, wherein said apparatus generates at least one chemical for sterilizing microbes.

9. A method as claimed in claim 1, wherein the temperature in the water system is in a range of 5–50° C.

10. A method as claimed in claim 1, wherein the surface of said sensor contacting the water is heated by a heater to the temperature higher than that of the water system.

11. A method as claimed in claim 10, wherein the surface of the sensor contacting the water is heated to 5–50° C. by said heater.

* * * * *